United States Patent
Bellier et al.

(10) Patent No.: US 12,428,625 B2
(45) Date of Patent: Sep. 30, 2025

(54) VIRUS-LIKE PARTICLES WHICH CAN BE USED IN THE TREATMENT OF ALLERGIES

(71) Applicants: Sorbonne Universite, Paris (FR); INSERM (Institut National de la Santé et de la Recherche Médicale), Paris (FR); Assistance Publique—Hôpitaux de Paris, Paris (FR)

(72) Inventors: Bertrand Bellier, Paris (FR); David Klatzmann, Paris (FR)

(73) Assignees: Sorbonne Universite, Paris (FR); INSERM (Institut National de la Santé et de la Recherche Médicale), Paris (FR); Assistance Publique—Hôpitaux de Paris, Paris (FR)

( * ) Notice: Subject to any disclaimer, the term of this patent is extended or adjusted under 35 U.S.C. 154(b) by 1371 days.

(21) Appl. No.: 16/759,591

(22) PCT Filed: Oct. 26, 2018

(86) PCT No.: PCT/FR2018/052674
§ 371 (c)(1),
(2) Date: Jun. 8, 2021

(87) PCT Pub. No.: WO2019/081872
PCT Pub. Date: May 2, 2019

(65) Prior Publication Data
US 2021/0299195 A1    Sep. 30, 2021

(30) Foreign Application Priority Data
Oct. 26, 2017 (FR) ...................... 1760110

(51) Int. Cl.
| | | |
|---|---|---|
| C12N 7/00 | (2006.01) |
| A61K 35/76 | (2015.01) |
| A61K 39/35 | (2006.01) |
| A61P 29/00 | (2006.01) |
| A61P 37/06 | (2006.01) |
| A61P 37/08 | (2006.01) |
| C07K 14/005 | (2006.01) |
| C07K 14/705 | (2006.01) |
| C12N 15/86 | (2006.01) |
| C12N 15/867 | (2006.01) |
| A61K 35/12 | (2015.01) |

(52) U.S. Cl.
CPC ............... *C12N 7/00* (2013.01); *A61K 35/76* (2013.01); *A61P 29/00* (2018.01); *A61P 37/08* (2018.01); *C07K 14/005* (2013.01); *C07K 14/70521* (2013.01); *C07K 14/70578* (2013.01); *C12N 15/86* (2013.01); *A61K 2035/122* (2013.01); *C12N 2740/13023* (2013.01); *C12N 2740/16023* (2013.01); *C12N 2740/16043* (2013.01)

(58) Field of Classification Search
None
See application file for complete search history.

(56) References Cited

FOREIGN PATENT DOCUMENTS

| CN | 101486997 A | 7/2009 |
|---|---|---|
| WO | WO-2008/130382 A2 | 10/2008 |
| WO | WO-2011/003905 A1 | 1/2011 |
| WO | WO-2016/128542 A1 | 8/2016 |

OTHER PUBLICATIONS

Skountzou et al. Incorporation of Glycosylphosphatidylinositol-Anchored Granulocyte-Macrophage Colony-Stimulating Factor or CD40 Ligand Enhances Immunogenicity of Chimeric Simian Immunodeficiency Virus-Like Particles. Journal of Virology, Feb. 2007, vol. 81, No. 3, p. 1083-1094.*
Leb et al. Modulation of allergen-specific T-lymphocyte function by virus-like particles decorated with HLA class II molecules. J Allergy Clin Immunol 2009;124:121-128.*
Kueng, et al. General Strategy for Decoration of Enveloped Viruses with Functionally Active Lipid-Modified Cytokines. Journal of Virology, Aug. 2007, p. 8666-8676 vol. 81, No. 16.*
Chen et al "Immunosuppression in Early Postnatal Days Induces Persistent and Allergen-Specific Immune Tolerance to Asthma in Adult Mice" PLoS One vol. 10, pp. 1-14, 2015.
Rolph et al "Loss of Antiviral Cytotoxic T-Lymphocyte Activity During High-Level Antigen Stimulation" Viral Immunology vol. 11, pp. 183-195, 1998.

* cited by examiner

*Primary Examiner* — Nianxiang Zou
(74) *Attorney, Agent, or Firm* — Morse, Barnes-Brown & Pendleton, P.C.; Martin Z. Zhang, Esq.; Russell L. Widom

(57) ABSTRACT

The invention relates to a virus-like particle comprising an allergen and an immunoregulatory molecule exposed on its surface. The invention also relates to the use of said particle in the treatment of an allergy.

13 Claims, 11 Drawing Sheets
Specification includes a Sequence Listing.

tVLP$^{OVA}$

VLP- / VLPGFP / tVLPGFP

Sorted dendritic cells
(CD11c_high; MHC-II_high) from
Balb/c mouse spleen OR
Bone marrow dendritic cells Co-culture
for 24 hours without LPS

SEQUENCE LISTING

<160> NUMBER OF SEQ ID NOS: 4

<210> SEQ ID NO 1
<211> LENGTH: 184
<212> TYPE: PRT
<213> ORGANISM: Mus musculus

<400> SEQUENCE: 1

-continued

```
Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

Val Phe Ser Glu Ala Ile Gln Val Thr Gln Pro Ser Val Val Leu Ala
        35                  40                  45

Ser Ser His Gly Val Ala Ser Phe Pro Cys Glu Tyr Ser Pro Ser His
    50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Thr Ala Val
            180

<210> SEQ ID NO 2
<211> LENGTH: 49
<212> TYPE: PRT
<213> ORGANISM: Vesicular stomatitis virus

<400> SEQUENCE: 2

Ser Ser Ile Ala Ser Phe Phe Phe Ile Ile Gly Leu Ile Ile Gly Leu
1               5                   10                  15

Phe Leu Val Leu Arg Val Gly Ile His Leu Cys Ile Lys Leu Lys His
            20                  25                  30

Thr Lys Lys Arg Gln Ile Tyr Thr Asp Ile Glu Met Asn Arg Leu Gly
        35                  40                  45

Lys

<210> SEQ ID NO 3
<211> LENGTH: 5
<212> TYPE: PRT
<213> ORGANISM: artificial sequence
<220> FEATURE:
<223> OTHER INFORMATION: Sequence flexible

<400> SEQUENCE: 3

Gly Gly Gly Gly Ser
1               5

<210> SEQ ID NO 4
<211> LENGTH: 30
<212> TYPE: PRT
<213> ORGANISM: Mus musculus
```

-continued

<400> SEQUENCE: 4

```
Met Arg Ala Gln Arg Gly Leu Ile Leu Leu Leu Leu Leu Leu Ala Val
1               5                   10                  15

Phe Cys Ser Thr Ala Val Ser Leu Thr Cys Tyr His Cys Phe
            20                  25                  30
```

VIRUS-LIKE PARTICLES WHICH CAN BE USED IN THE TREATMENT OF ALLERGIES

FIELD OF THE INVENTION

The invention relates to compositions comprising virus-like particles useful for modifying, regulating or suppressing an immune response, more particularly for treating an immune dysfunction such as an allergy. Methods for producing said compositions are described. This invention can be used in mammals, in particular in humans but also in other vertebrates.

PRIOR ART

The prevalence of immune dysfunctions, including allergic diseases (atopic dermatitis, asthma, rhinitis, conjunctivitis and food allergy), has increased considerably in industrialized countries in recent decades. Both allergies and autoimmune diseases result from a dysfunction of the immune system. The allergic reaction is an immediate hypersensitivity response which is the consequence of the interaction of the allergen with IgE antibodies attached to basophilic and eosinophilic mast cells and granulocytes. This interaction results in the release of mediators such as histamine, cytokines and proteases within minutes. This first phase, dependent on IgE produced by Th2 T-lymphocytes, may then be followed by a delayed reaction due to the activation of other allergen-specific T cells and the production of pro-inflammatory cytokines. This reaction thus leads to chronic forms of allergic inflammation.

Although various medicinal products are available to treat symptoms, no specific acting treatment is available. There is no effective method for the long-term and safe treatment of allergy today. For example, desensitization methods consisting of the progressive administration of allergens to a subject to induce specific immune tolerance are not very effective in the long term and can lead to anaphylactic shock or severe allergic reactions. The development of new effective and specific treatments for immune dysfunctions therefore remains necessary.

Virus-like particles (VLP) are used for anti-infectious or anti-tumor vaccination. Virus-like particles have the advantage that they can be easily modulated and can be used as an antigenic platform. Targeted antigens can thus be carried inside or on the surface of the virus-like particles, helping to trigger specific humoral and cellular immune responses, but also masking the antigens from neutralizing or reactive factors (IgE) when they are inside. In addition, the great flexibility of this antigenic platform allows the vectorization of immunoregulatory molecules.

SUMMARY OF THE INVENTION

Interestingly, the inventors have shown that virus-like particles can block the activation of antigen presenting cells and the activation of T cells and can therefore be used to modulate antigen-specific immune responses or even induce specific immune tolerance. In other words, virus-like particles make it possible to make the body tolerant to the antigens vectorized by these so-called tolerogenic virus-like particles.

A first object of the invention is a virus-like particle comprising one or more antigen(s) and an immunoregulatory molecule exposed on the surface of the particle. The virus-like particle according to the invention is particularly used in the treatment of an allergy.

The virus-like particle is preferably in the form of a pharmaceutical composition further comprising a pharmaceutical excipient.

According to another aspect of the invention, a plasmid or set of plasmid(s) capable of producing in situ a virus-like particle as defined herein is used, in particular for their use in the treatment of an immune dysfunction, such as allergy.

FIGURE LEGEND

Figure 1:
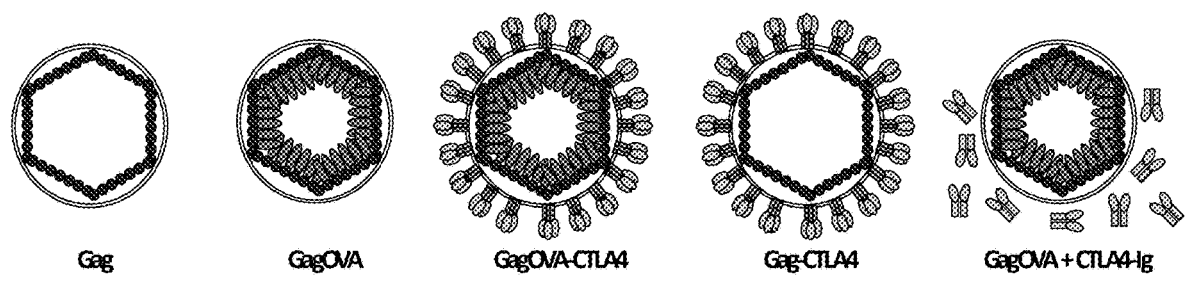
FIG. 1 illustrates the structure of VLP without antigen and without CTLA-4 (VLP), VLP with OVA antigen alone (VLP$^{OVA}$) or combined with CTLA-4 (tVLP$^{OVA}$), VLP without antigen and expressing CTLA-4 on its surface (tVLP-), and VLP with OVA antigen (VLP$^{OVA}$) co-injected with soluble CTLA-4 (CTLA-4-Ig).
Figure 2A:
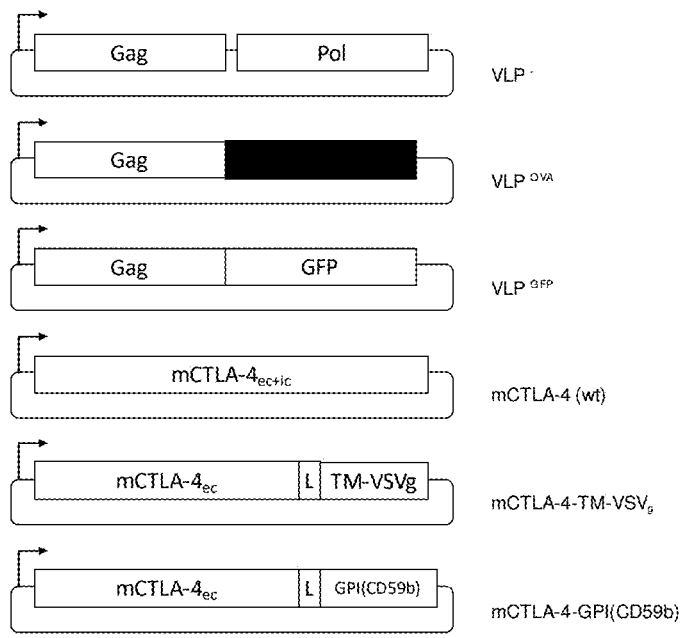
FIGS. 2A and 2B illustrate the constructs used to form the particles according to the invention (FIG. 2A) and the structure of the tolerogenic virus-like particle tVLP$^{OVA}$ (FIG. 2B) where OVA is the target antigen.
Figure 2B:
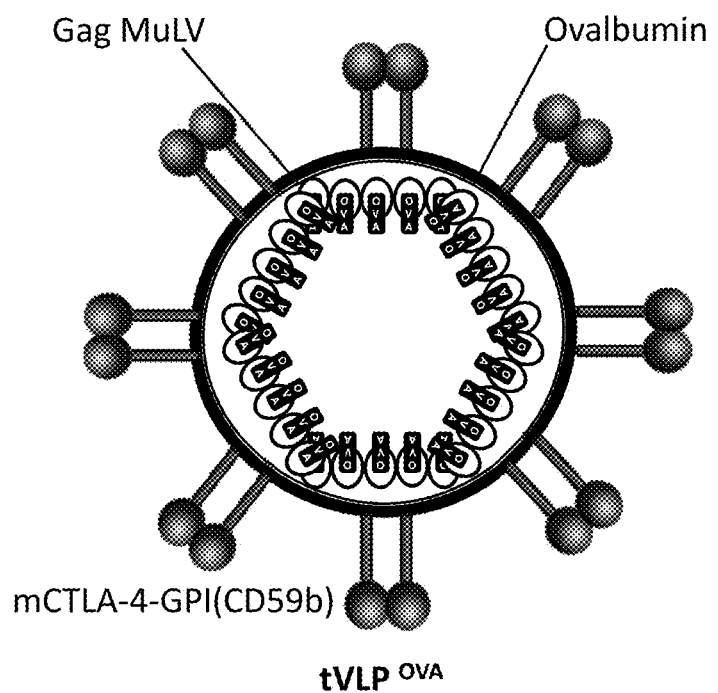
Figure 3A:
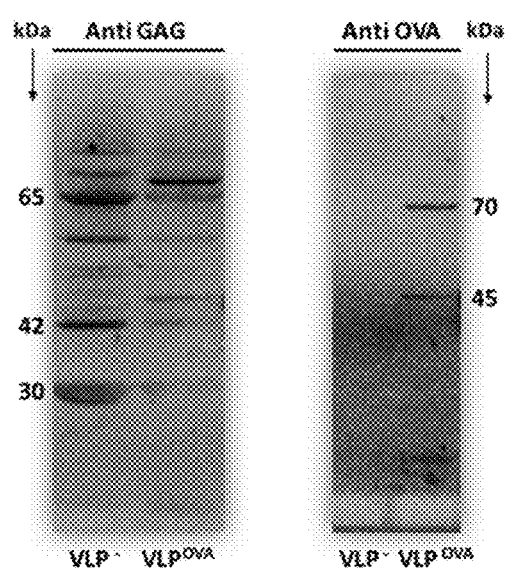
Figure 3B:
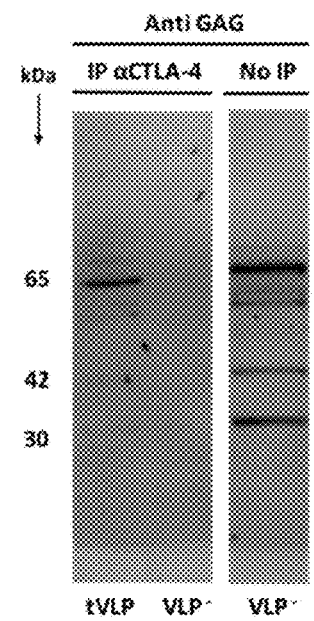
Figure 3C:
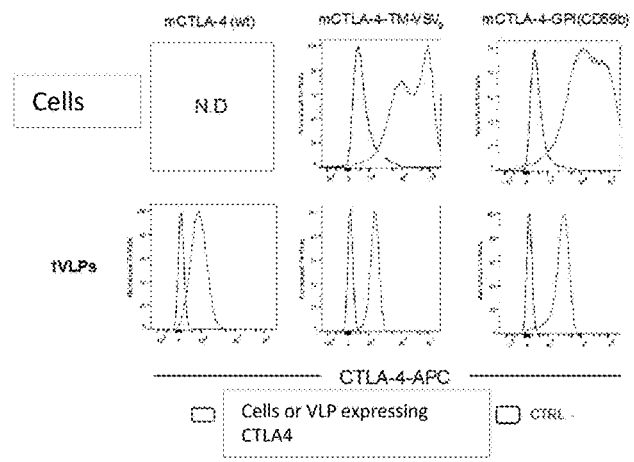
Figure 3D:
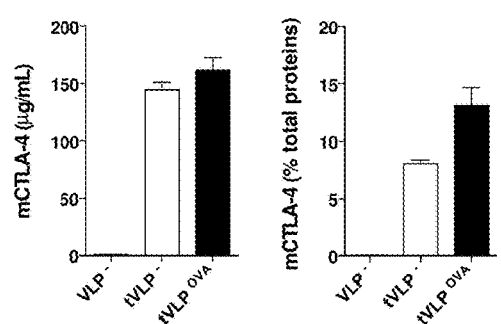

FIGS. 3A-3D illustrate the characterization and expression of therapeutic proteins in tVLP$^{OVA}$. FIG. 3A. Western blot validation of Gag and OVA expression in virus-like particles VLP$^{OVA}$. VLP- are control particles without OVA antigen. FIG. 3B. Validation by immunoprecipitation of CTLA-4 expression in tVLP virus-like particles. FIG. 3C. Comparison of the expression of chimeric forms of CTLA-4 (WT, TM-VSV-G, or GPI anchor domain) in transfected cells (top) or on the surface of virus-like particles (bottom) by flow cytometry. Non-transfected cells or VLP—are used as the negative control (black). FIG. 3D. Quantification of the CTLA-4 domain in tVLP, tVLP$^{OVA}$ or VLP- preparations by ELISA (left) and relative quantification of CTLA-4 to total proteins measured using the BCA method (right). Results are mean±SEM (n=4) and represent 3 independent experiments.

Figure 4A:
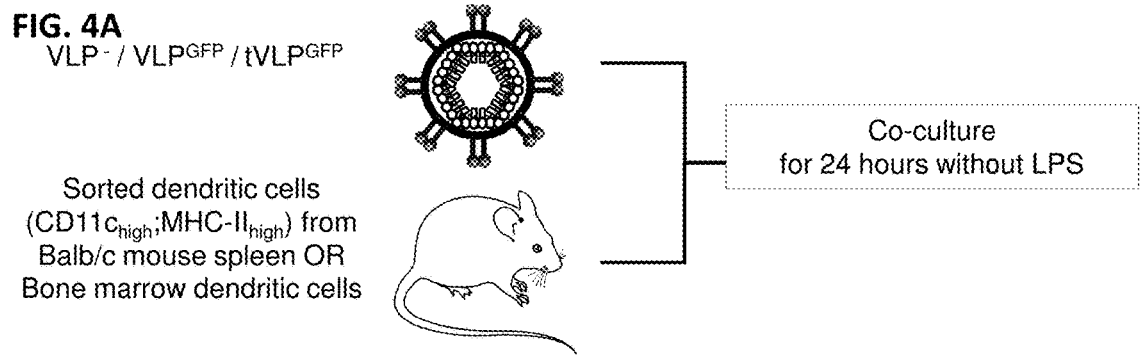
Figure 4B:
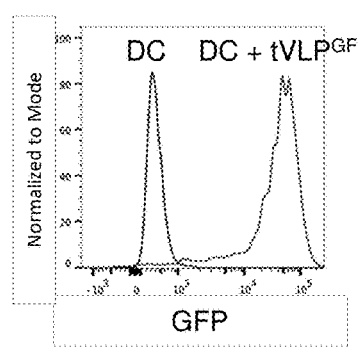
Figure 4C:
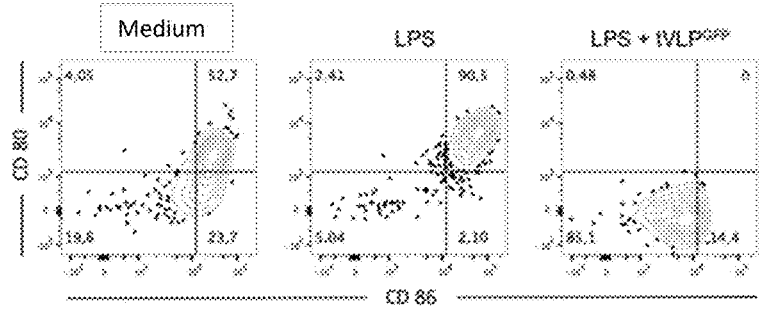
Figure 4D:
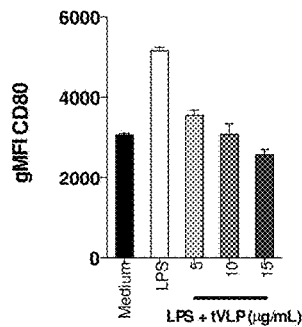
Figure 4D:
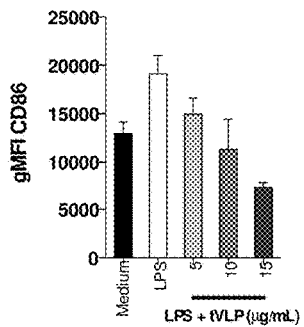
Figure 4E:
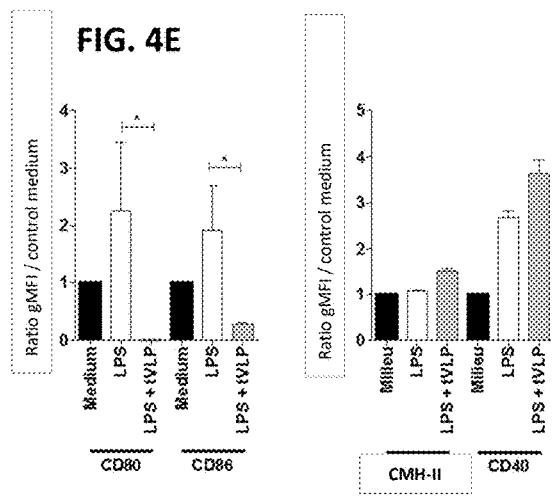

FIGS. 4A-4E illustrate the uptake and effects of tVLP on purified dendritic cells. FIG. 4A. Experimental design. Purified CD11c$^{high}$ MHC-II$^{high}$ dendritic cells from the spleen of BALB/c mice or dendritic cells from bone marrow are cultured in the presence of VLP-, VLP$^{GFP}$ or tVLP$^{GFP}$ and stimulated or not with LPS. Twenty-four hours after culture, the expression of co-stimulation molecules and activation markers is analyzed by flow cytometry. FIG. 4B. The uptake of tVLP$^{GFP}$ by purified dendritic cells is confirmed by the presence of GFP$^+$ cells after 24 hours of culture. The VLP are used as a negative control (black). (FIGS. 4C-4E). The expression of co-stimulation molecules and activation markers is analyzed by flow cytometry on purified dendritic cells after co-culture with medium in the presence or not of 1 µg/mL LPS and 5, 10 or 15 µg/mL tVLP$^{GFP}$. The expression of CD80, CD86, CD40 and MHC-II is analyzed in living cells expressing CD11c and MHC-II. FIG. 4C. Represents the cytometric profiles of CD80, CD86 in dendritic cells cultured in culture medium alone, in the presence of LPS and tVLP$^{GFP}$ (15 µg/mL). FIG. 4D. The expression of co-stimulation molecules is measured using the geometric mean fluorescence (MFI). FIG. 4E. Expression modulation is represented by the MFI ratio compared to the control medium.

Figure 5A:
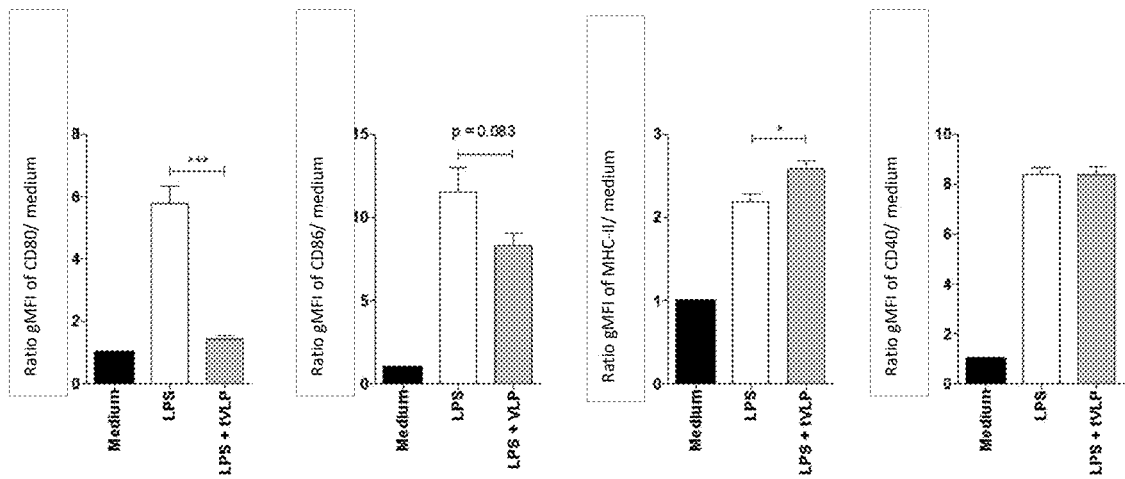
Figure 5B:
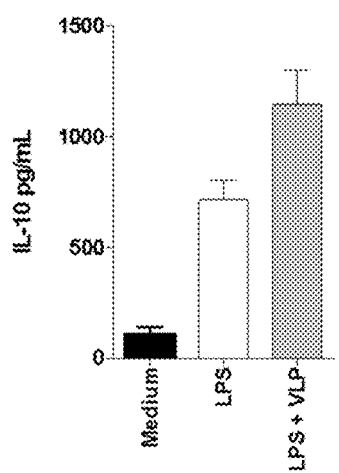

FIGS. 5A and 5B illustrate the effects of tVLP on dendritic cells derived from bone marrow precursors. FIG. 5A. illustrates CD80, CD86, CD40 and MHC-II expression analyzed by flow cytometry on live bone marrow-derived dendritic cells after co-culture with medium with or without the presence of 1 µg/mL LPS and 5, 10 or 15 µg/mL tVLP$^{GFP}$. The expression modulation of CD80, CD86, CD40 and MHC-II is represented by the gMFI ratio compared to the control medium. FIG. 5B. Quantification by ELISA of IL-10 in the culture supernatant of dendritic cells after 24 hours culture in medium alone, in the presence of LPS or in the presence of LPS and tVLP.

Figure 6A:
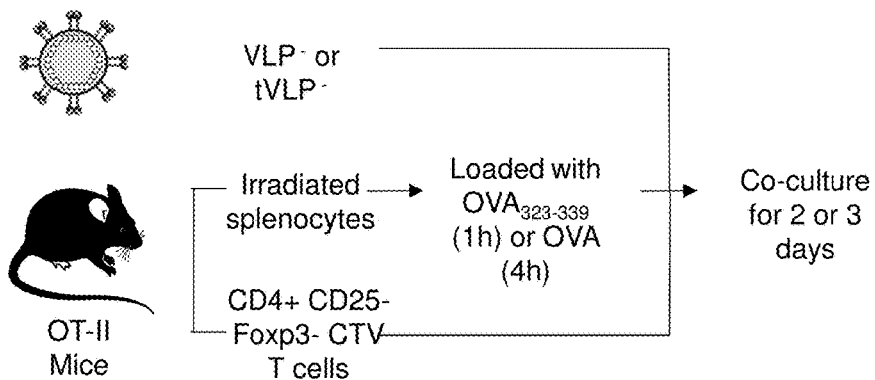
Figure 6B:
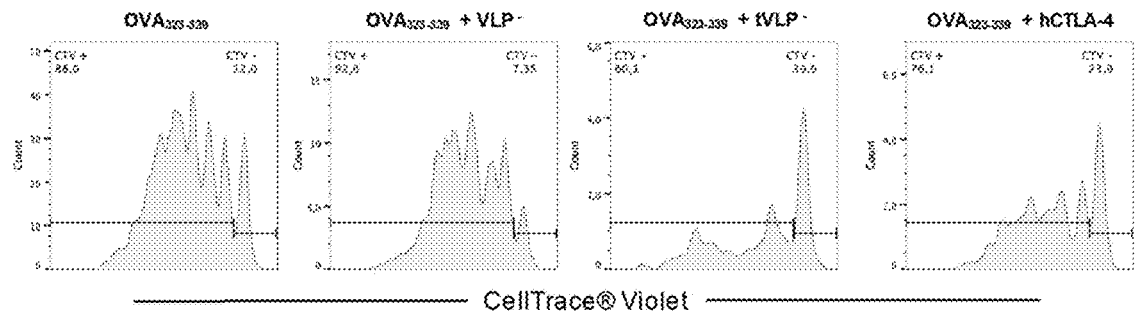
Figure 6C:
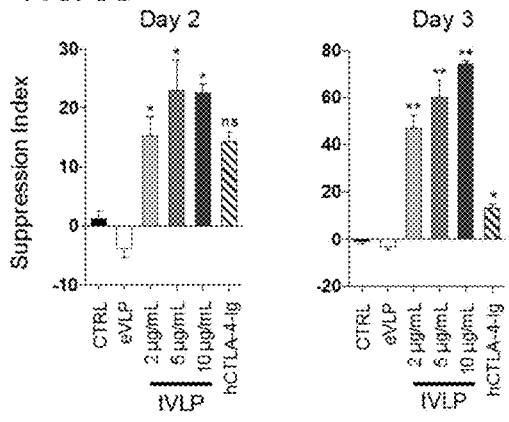
Figure 6D:
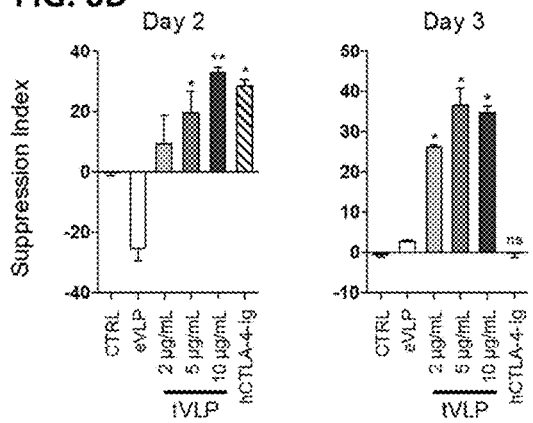

FIGS. 6A-6D illustrate the blocking of antigen-specific T cell proliferation by tVLP. FIG. 6A. Experimental design. CD4+CD25-T cells from OT-II mice are cultured for 2-3 days with irradiated spleens from OT-II mice loaded with an $OVA_{323-339}$ peptide or OVA protein. To analyze proliferation, CD4+OT-II T cells are labeled with CellTrace® Violet. Live OT-II CTV+CD4+ T cells co-cultured for 2 days with irradiated splenocytes loaded with an $OVA_{323-339}$ peptide in the presence or absence of 10 μg/mL of VLP⁻, tVLP⁻, or an equivalent dose of hCTLA-4 are analyzed by flow cytometry. FIG. 6B. Cytometric profile of CTV dilutions of $CD4^+$ $CTV^+$ OT-II T cells after two days under different culture conditions. (FIGS. 6C and 6D). Suppression indices of CTV dilutions of OT-II cells co-cultured for two or three days with splenocytes contacted with $OVA_{323-339}$ peptide (FIG. 6C) or OVA protein (FIG. 6D). Results are mean±SEM (n=4) and represent 3 independent experiments.

Figure 7A:
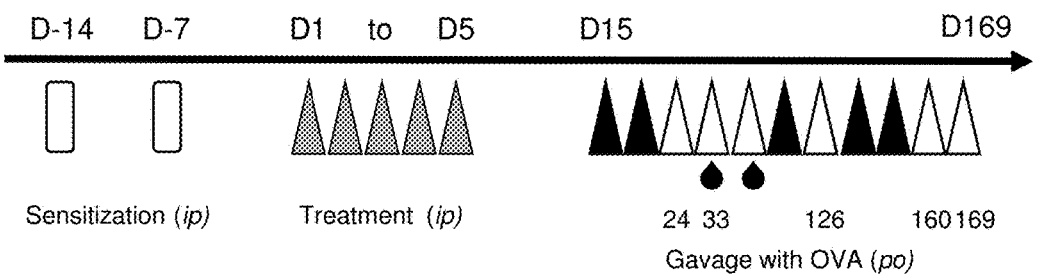
Figure 7B:
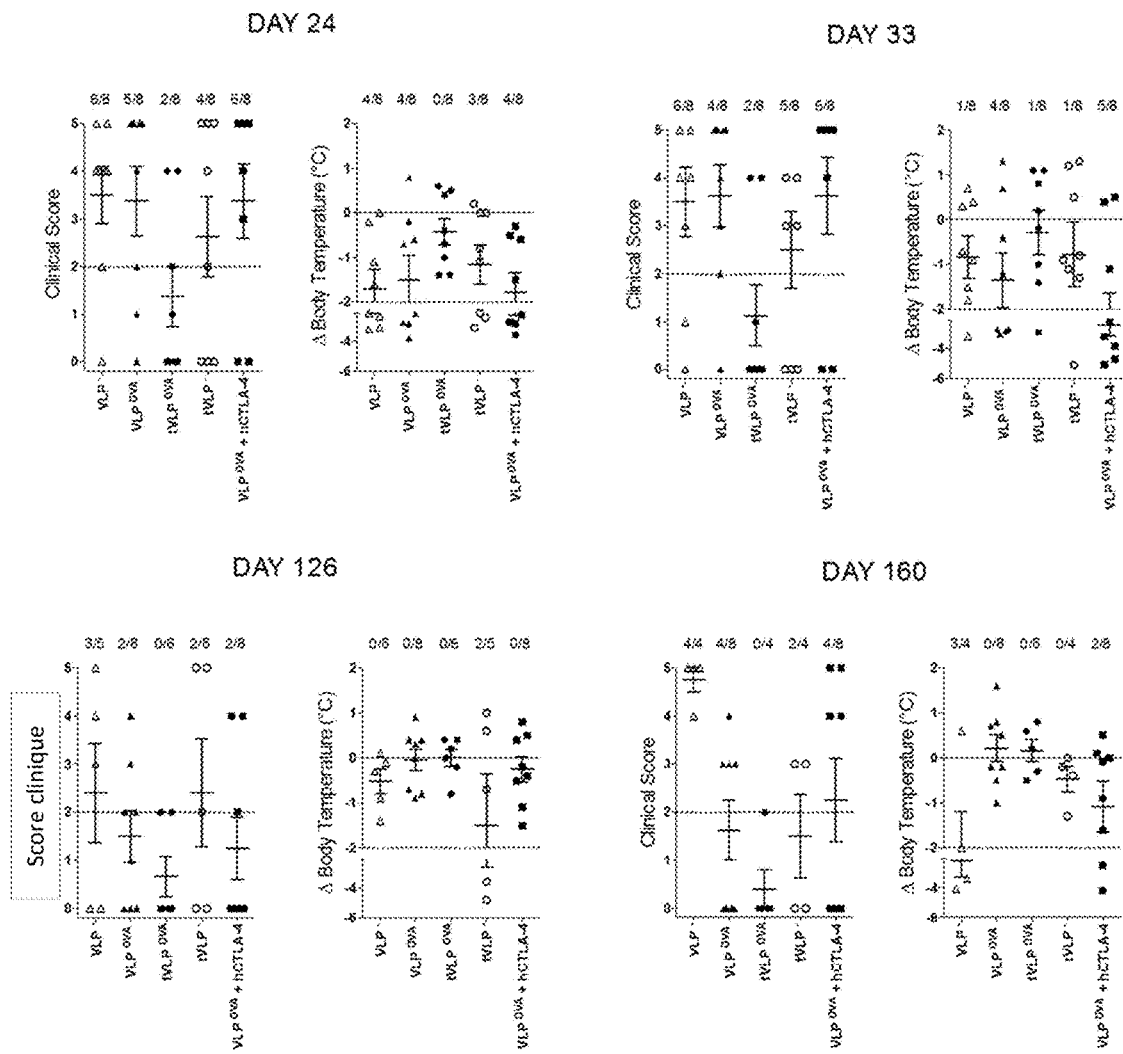
Figure 7C:
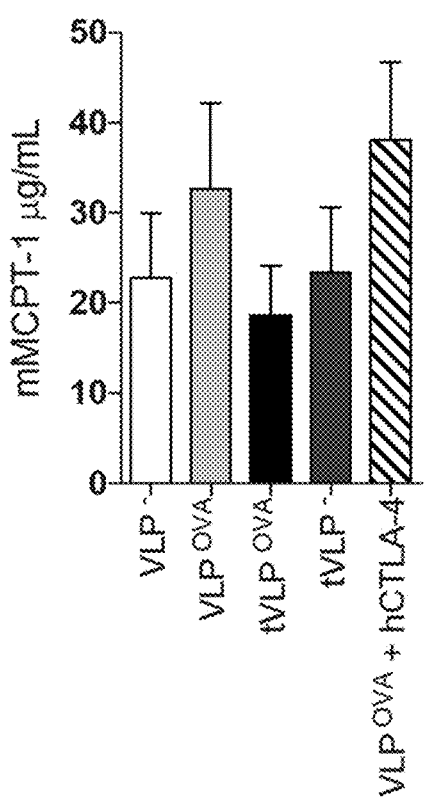
Figure 7D:
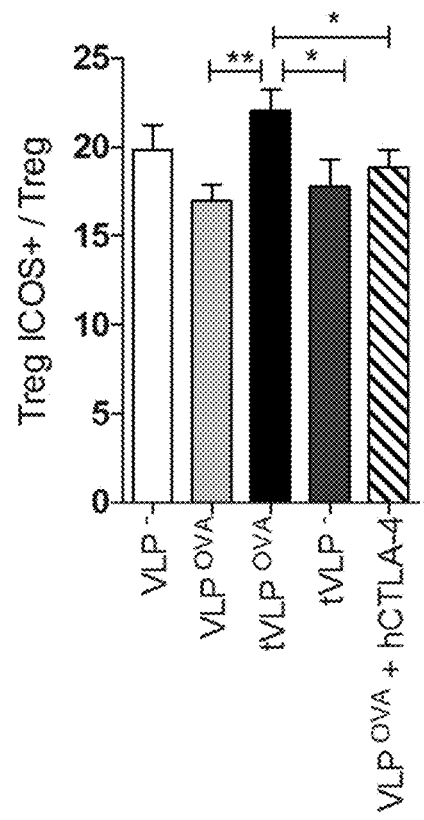

FIGS. 7A-7D illustrate the protective effect of $tVLP^{OVA}$ in the development of food allergy. FIG. 7A. Experimental design: Five groups of mice were sensitized at D-14 and 7 to OVA and treated daily for 5 days intraperitoneally with VLP⁻, $VLP^{OVA}$, $tVLP^{OVA}$, tVLP⁻ or $VLP^{OVA}$+hCTLA-4 (30 μg/gavage). At D10, the mice are gavaged every other day by oral administration of OVA and the severity of allergic reactions is measured after the fifth gavage. The mice are then re-gavaged with OVA every 9 to 12 days until a score above 4 is obtained for 80% of the mice in the control group. At D33 and D45, peripheral blood is drawn 30 min after sensitization. FIG. 7B. Food allergy was assessed by a change in core temperature measured 30 minutes after oral gavage. Diarrheal stool (score 0 to 3) and shaggy coat (score 0 to 2) were assessed quantitatively. The clinical score (diarrhea score and coat score) and temporal temperature change are given for each mouse at D24, D33, D126 and D160. The dashed line delineates clinical symptoms and severe temperature drop. (FIGS. 7C and 7D). The level of MCPT-1 in peripheral blood is measured at D33 (FIG. 7C) and the percentage of ICOS+Tregs (CD4+, CD25+, Foxp3+) is measured at D45 (FIG. 7D). Tregs are defined as expressing CD4, CD25 and Foxp3.

Figure 8A:
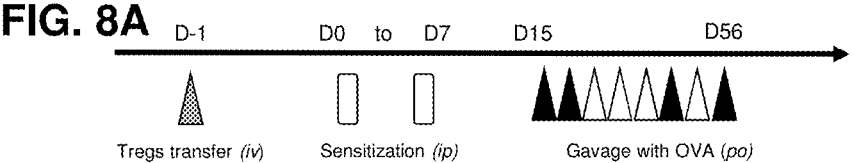
Figure 8B:
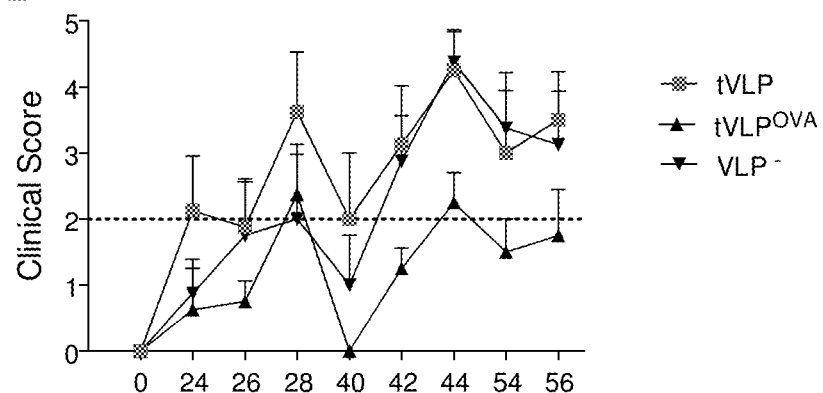
Figure 8C:
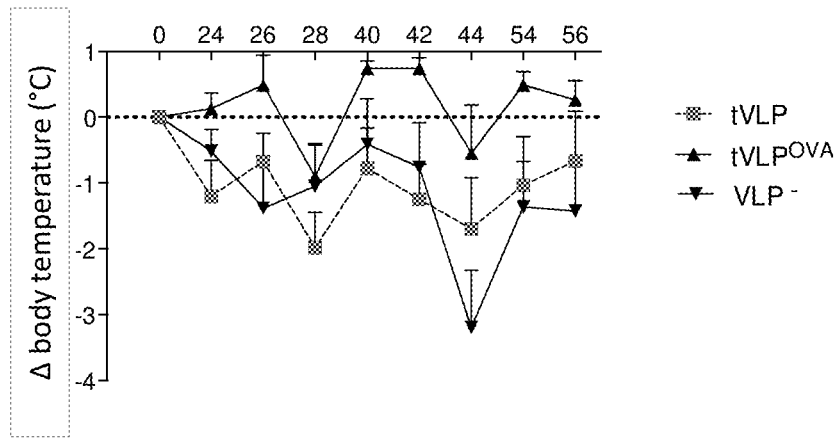

FIGS. 8A-8C illustrate the control of OVA-specific allergic responses by in vivo transfer of Treg from mice treated with $tVLP^{OVA}$. FIG. 8A. Experimental design: three groups of BALB/c mice are injected with 50,000 Tregs from mice treated with tVLP, $tVLP^{OVA}$ or VLP⁻. Three days later, the mice were sensitized by two injections of OVA/alum (Day 0 and 7) and gavaged five times (every other day). Gavage is then carried out every 9 to 12 days. Clinical score (FIG. 8B) and body temperature change (FIG. 8C) are assessed 30 minutes after oral gavage. The curves represent the mean of each group and the bars represent the standard deviation. Statistical data are obtained with the VLP control group.

Figure 9A:
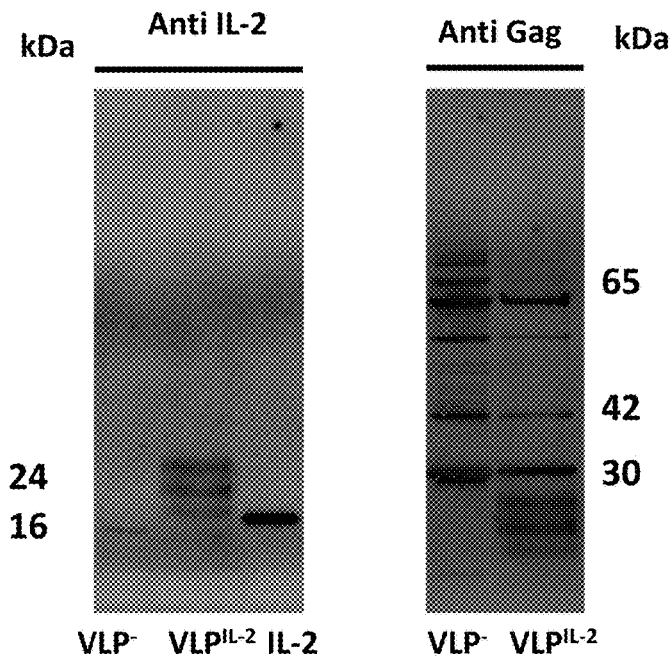
Figure 9B:
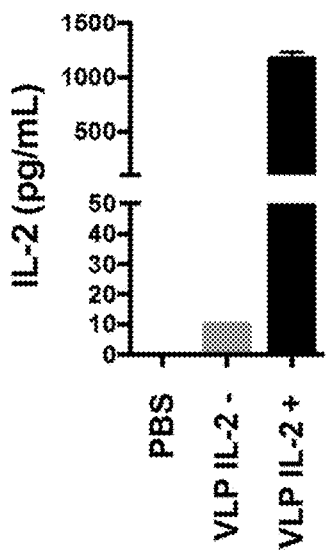
Figure 9C:
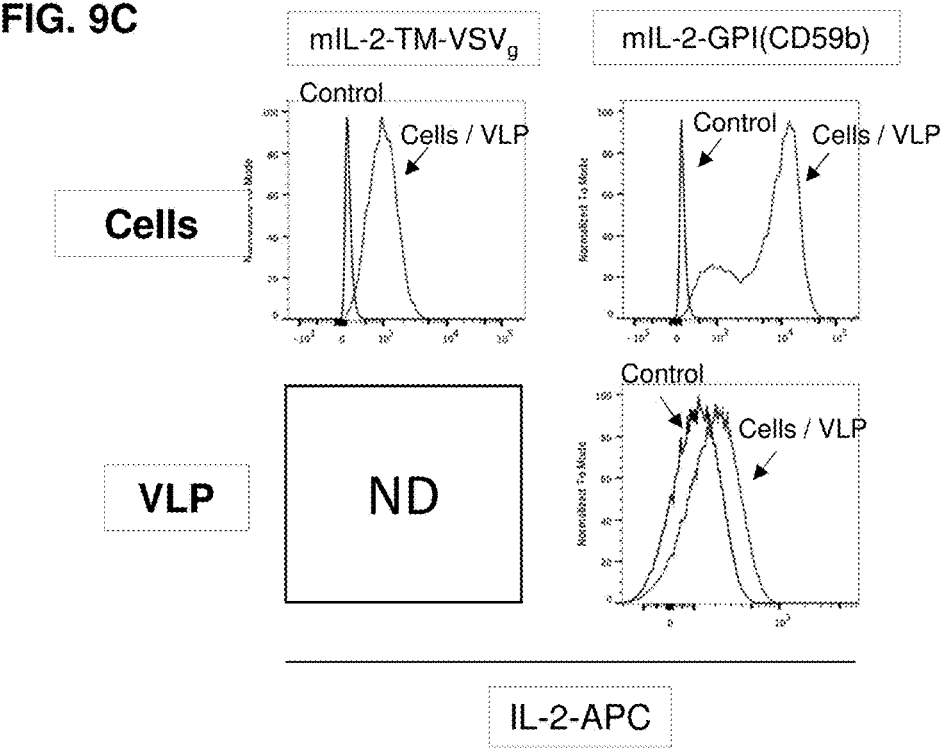

FIGS. 9A-9C illustrate the characterization and expression of therapeutic proteins in tVLP expressing IL-2 as an immunoregulatory molecule. FIG. 9A. Western blot validation of IL-2 and Gag expression in virus-like particles. FIG. 9B. Quantification of IL-2 in IL-2⁺ and IL-2-VLP preparations by ELISA. FIG. 9C. Comparison of the expression of chimeric forms of IL-2 (TM-VSV-G or GPI anchor domain) in transfected cells (top) or on the surface of virus-like particles (bottom) by flow cytometry. Non-transfected cells or VLP are used as the negative control (black).

Figure 10A:
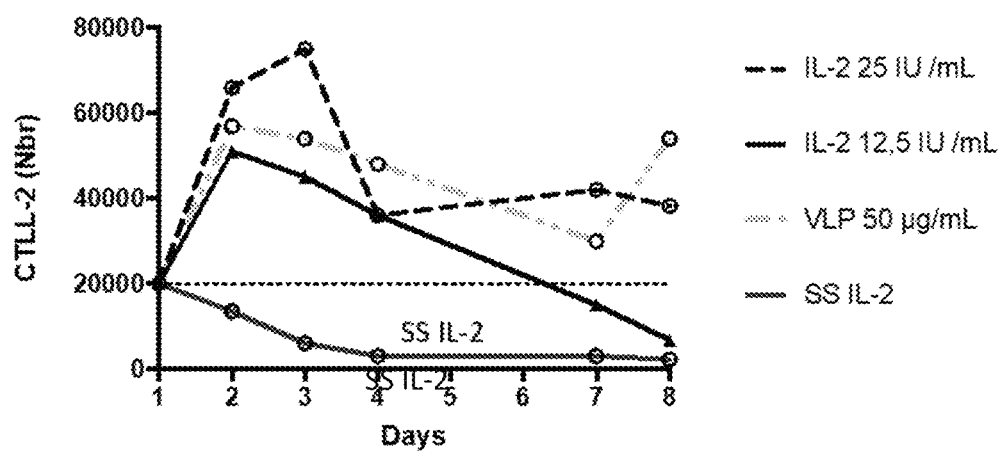
Figure 10B:
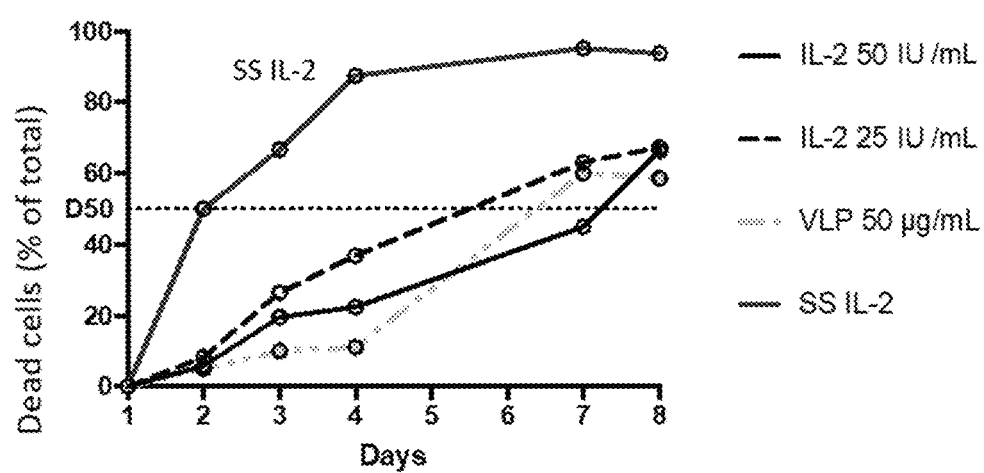

FIGS. 10A and 10B illustrate the functional validation of IL-2 present on the surface of tVLP. The IL-2+VLP were cultured (50 μg/mL) with IL-2-dependent CTLL-2 cells. Cell proliferation (FIG. 10A) and survival (FIG. 10B) were evaluated over an 8-day period. In control, IL-2 at 25 or 50 IU/mL, or medium alone was used.

DETAILED DESCRIPTION OF THE INVENTION

The inventors developed a method for treating immune dysfunctions in a subject, such as allergies, comprising the administration of virus-like particles containing an antigen and an immunoregulatory molecule.

This virus-like particle advantageously contains an immunoregulatory molecule exposed on its surface.

The present invention therefore relates to a virus-like particle comprising an antigen and an immunoregulatory molecule exposed on the surface of the particle, which makes it possible to promote the specific tolerance of the antigen. The immunoregulatory molecule is preferably a molecule which exerts regulatory and/or suppressive functions on antigen presenting cells, promoting recruitment of regulatory T cells. In particular, the immunoregulatory molecule may be an immune-checkpoint receptor, more particularly a peptide sequence comprising the extracellular domain, more particularly the Ig-like domain of an immune-checkpoint receptor, preferably selected from the group consisting of: CTLA-4 (cytotoxic T-lymphocyte-associated protein 4), OX40 (tumor necrosis factor receptor superfamily, member 4 (TNFRSF4)), PD1 (programmed cell death 1), Tim3 (also known as HAVCR2), and LAG-3 and TIGIT (also known as IVSTM3). The immunoregulatory molecule may also be a cytokine such as IL-2 (interleukin 2), IL-10 (interleukin 10) and TGF-beta. The immunoregulatory molecule is preferably fused to the transmembrane and/or anchoring domain of a protein, preferably a glycoprotein. In particular the immunoregulatory molecule is bound to the transmembrane domain of an envelope protein or a glycosylphosphatidylinositol (GPI) anchoring system to be exposed to the surface of the particle. The cytokine, which is preferably interleukin 2, may be human or from another animal species, it may be wild or mutant. In particular it may be a modified human IL-2 des-alanyl-1, serine-125.

It is possible to associate "adjuvant" molecules with the ability to direct immune responses towards a desired cytokine profile. A molecule capable of activating TLR (toll-like receptor) such as viral RNA, preferably non-coding RNA, can be associated to enhance Th1 responses and thus combat Th2 responses associated with allergy (Pitoiset F. et al. J. Virol. 2017 Oct. 13; 91 (21).

The virus-like particle is preferably a synthetic retroviral particle. In other words, the virus-like particle comprises a retroviral capsid protein and/or a retroviral envelope protein.

The present invention relates more particularly to the virus-like particles defined herein, for use in the treatment of immune dysfunction.

The virus-like particle of said invention comprises an antigen which is an allergen, in particular for use in the treatment of allergy, preferably a food allergy.

In particular, the virus-like particles can be used for allergic desensitization. Thus, a progressive administration or repeated administrations of virus-like particles comprising the allergen makes it possible to induce a specific tolerance to this allergen by inducing regulatory cells and suppressing the specific response and a polarization of the immune response towards a different Th2 profile.

The present invention also relates to one or more plasmid(s) capable of producing virus-like particles in vitro and in situ. In particular, use is made of one or more plasmids encoding a capsid protein and/or an envelope protein constituting the virus-like particle. The present invention relates more particularly to said plasmids for use in the treatment of immune dysfunction.

The virus-like particle or the plasmid(s) capable of producing a virus-like particle in situ may be administered to the subject preferably by mucosal route, for example oral, sublingual, intranasal, subcutaneous or intravenous.

The present invention uses a pharmaceutical composition comprising the virus-like particle or plasmid(s) capable of producing virus-like particles in situ. This composition may also include a pharmaceutical excipient.

The pharmaceutical composition may comprise several virus-like particles or several plasmid(s) capable of producing in situ virus-like particles comprising different antigens and/or different immunoregulatory molecules.

Also described here is a method for preparing virus-like particles or plasmids capable of producing the virus-like particles in situ.

Definitions

The term "antigen" refers to a molecule such as a protein, polypeptide, peptide, lipid, nucleic acid, polysaccharide, epitope capable of being recognized by an antibody or cells of the immune system. In particular the antigen is capable of triggering an immune response. The immune response may lead to antibody production and/or activation of cells of the immune system. In particular, the antigen is a heterologous protein, polypeptide, peptide of the virus-like particle, especially a non-viral protein, polypeptide or peptide. In the context of the present invention, the antigen is a molecule heterologous to the virus forming the particle. It is preferably a non-viral molecule. The term also includes epitopic fragments of complete proteins.

Allergic reactions or symptoms may include rhinitis, allergic asthma, dermatitis, hives, sinus inflammation or anaphylactic shock following exposure to the allergen. The allergic reaction is for example characterized by an immune response directed against the allergen, associated with an increase in IgE production and/or an increase in the production of allergen-specific immunoglobins. Anaphylactic shock is a violent allergic reaction causing a severe disruption of the blood circulation with a very sudden drop in blood pressure endangering vital organs.

Allergens as defined herein include antigens capable of stimulating an allergic reaction in a subject. Allergens may be contained in or derived from foods such as milk, eggs, sesame, wheat, soy, fish, seafood, peanuts, nuts. Allergens may also be contained in or derived from non-food products such as dust mites, pollen, insect stings, animal fur, wool, medicines, etc. The allergens present in the virus-like particles used here are preferably peptides or polypeptides or proteins forming all or part of an antigen capable of being recognized by a cell of the immune system, and in respect of which tolerance to the allergen is sought.

The term "treat" means to suppress the symptoms, eliminate the causes of the symptoms either transiently or permanently, but also to prevent or slow down the onset of symptoms of immune dysfunction. In particular, in the context of allergy treatment, the term "treat" means to suppress the symptoms of the allergy such as rhinitis, allergic asthma, dermatitis, hives, sinus inflammation or anaphylactic shock. It also means reducing the risk of occurrence or severity of the allergic response. The term "treat" also includes desensitizing the individual, also called allergy immunotherapy, allowing the individual to become tolerant to a particular allergen over the long term.

The term "subject" means any human person or non-human animal that is likely to be treated by the composition of the present invention. In particular, subjects who are susceptible to immune dysfunction, subjects who have previously been subject to immune dysfunction, subjects who have a predisposition to immune dysfunction or subjects who show signs of immune dysfunction.

For the purposes of the present invention, the expression "effective amount" (or "therapeutically effective amount") refers to an amount of virus-like particles according to the invention necessary or sufficient to, without causing significant and unfavorable side effects for the subject, delay or stop the occurrence of an immune dysfunction, bring about improvements, reduce the severity or incidence of an immune dysfunction, or stop or cure an immune dysfunction. An effective amount may be administered prior to the onset of immune dysfunction for prophylactic or preventive action. Alternatively or additionally, an effective amount may be administered after the onset of immune dysfunction for therapeutic action.

An "excipient" means, in the present invention, any substance other than the active ingredient present in a composition conferring on it properties of stability, form (liquid, solid, capsule, etc., according to the mode of administration), taste, dissolution (for example targeted dissolution in the stomach or digestive tract), color, etc. A "pharmaceutically acceptable excipient" means more specifically an excipient which does not induce an undesirable reaction when it is administered to a subject, preferably a human. This definition includes all solvents, dispersion media, coatings, antibacterial or antifungal agents, isotonic agents and agents which delay the absorption of the active ingredient, etc. For administration to humans, the preparations must meet sterility, pyrogenicity, general safety and purity standards defined by regulatory agencies, such as the FDA's Bureau of Biological Standards.

"RNA" here means any ribonucleic acid molecule. Ribonucleic acid molecules may be natural or modified ribonucleotides, in particular to be more resistant to RNases. The RNA sequence may include stabilizing sequences that increase the half-life of the RNA in the cytosol. For example, stabilizing sequences are transcribed and untranslated sequences of the β-globin gene.

The present invention relates to a virus-like particle comprising an antigen. The virus-like particle of the present invention is intended to durably and specifically regulate the immune system, in particular to block allergic responses and/or to reduce the level of IgE present in the serum of a subject exposed to an allergen and/or to generate suppressor lymphocytes capable of controlling allergic responses and/or to deviate the immune profile towards a non-Th2 profile. In order to promote specific tolerance of the antigen, the virus-like particle of the invention further comprises an immunoregulatory molecule expressed on the surface of the particle.

Virus-Like Particles Useful in the Invention:

The virus-like particles are formed by self-assembly of at least one structural protein of viral origin such as the capsid protein or the envelope protein. These particles mimic the structure and antigenic properties of the native virion, but are unable to replicate. In particular, the virus-like particles are produced by self-assembly of structural proteins, in particular of the constituent subunits of the viral capsid and/or envelope (international patent application WO2002/34893).

According to the invention, the virus-like particles can be obtained from double-stranded DNA viruses such as herpes virus, adenovirus, parvovirus, single-stranded DNA viruses, double-stranded RNA viruses such as reoviruses, positive polarity single-stranded RNA viruses, negative polarity single-stranded RNA viruses, retroviruses. In particular the virus-like particles are obtained from the assembly of structural proteins of AAV, adenoviruses, VSV, herpes viruses.

In a particular case, the virus-like particles can be prepared from retroviruses. These may include retroviruses belonging to the family of oncoviruses, lentiviruses or spumaviruses. Within the family of oncoviruses, these include slow, non-oncogenic oncoviruses, such as MoMLV, ALV, BLV, or MMTV, and fast oncoviruses, such as RSV. Examples of lentiviruses are HIV, SIV, IVF, or CAEV.

In another particular case, the viral particle according to the invention comprises a structural protein, preferably an envelope derived from VSV (vesicular stomatitis virus), more particularly VSV-G.

The structural proteins of said virus-like particle are capsids and/or viral envelopes. The viral capsid is a multi-protein structure that encloses and protects the genetic material in a virus. The capsid is formed from copies of a single or different protein subunits. Some viruses are surrounded by a lipid bilayer envelope containing glycoproteins. This envelope helps modulate tropism and immunogenicity.

In a preferred embodiment of the invention, the virus-like particle is a synthetic retroviral particle. A retroviral particle comprises an envelope protein synthesized from an env gene, capsid proteins synthesized from the gag gene, and enzymes such as reverse transcriptase, proteases or integrase synthesized from the pol gene, associated with a viral genome consisting of two copies of RNA containing the gag/pol/env sequences. The synthetic retroviral particle comprises an envelope protein and/or a capsid protein. In particular envelopes which can be used in the present invention are envelopes of the following viruses: 4070A, RD114, 10A1, VSV, LCMV, HIV, rabies virus, or GALV. In a preferred approach to the invention, the envelope has a tropism for mammalian cells, more particularly, for human cells. In a particular aspect of the invention, the virus-like particle does not include an envelope protein.

In particular, the virus-like particle comprises the MoMLV capsid gag protein capable of self-assembling into virus-like particles.

The virus-like particles may include modified viral proteins. These proteins can be modified by, among other things, bank screening, chemical modification or genetic modification of the sequence of the natural viral protein. For example, the viral protein may be modified by amino acid substitution, addition or deletion. Viral proteins may also be covalently or non-covalently bound to the antigen and/or immunoregulatory molecule by genetic modification of the sequence of the viral protein or by chemical binding. For example, the modified viral protein may include at least a portion of the viral protein fused to the antigen or immunoregulatory molecule.

In the present invention, the virus-like particle comprises an antigen. In particular, the antigen may be an allergen. The antigen may be exposed on the surface of the virus-like particle or contained in the virus-like particle. The antigen may be associated with the virus-like particle for example through the envelope, a fragment of the envelope, the capsid protein, a fragment of the capsid protein. In particular, the antigen can be fused through the N-terminal or C-terminal domain of the capsid protein or the fragment of the capsid protein to be contained in the virus-like particle. The antigen may also be fused to the transmembrane or anchor domain of the envelope or envelope fragment or to the GPI domain to be exposed on the surface of the virus-like particle.

In another particular embodiment, the antigen can be contained in the virus-like particle, for example by fusing the antigen to the capsid, in particular to the N- or C-terminal domain of the capsid, preferably to the C-terminal domain of the capsid protein. The antigen can be bound to the structural protein directly or via a "linker", preferably a peptide sequence. Peptide sequence means an amino acid sequence which makes it possible to bind protein subunits in such a way that the protein adopts a good conformation for the activity of the protein subunits. In particular, the "linker" peptide sequence is a sequence of 1, 2, 3, 4, 5, 10, 15, 20, 30, 40 or 50 amino acids.

In a preferred embodiment, the antigen may be contained within the virus-like particle for the treatment of allergy to avoid anaphylactic shock. For example, in order for the antigen to be contained within the particle, the antigen may be fused directly or via a peptide bond to the capsid protein, preferably to the C-terminal domain of the gag capsid protein. The antigen can also be exposed on the surface of the particle or contained within the particle by means of a chemical or enzymatic reaction.

In order to promote the specific tolerance of the antigen, the virus-like particle used in the invention comprises an immunoregulatory molecule.

Immunoregulatory molecules are capable of modulating the immune response, in particular by modulating the functions of antigen presenting cells and/or regulatory T cells. In a particular embodiment of the invention, immunoregulatory molecules are molecules capable of increasing the activity of regulatory T cells (Tregs).

In a particular embodiment, the immunoregulatory molecule may be a receptor capable of modulating the immune response, in particular, capable of inducing the suppressive function of Tregs. As an example, these immunoregulatory molecules can be derived from immune-check-point receptors such as PD1 (programmed cell death 1), also known as PDCD1 or CD279), CTLA-4 (cytotoxic T-lymphocyte antigen 4, also known as CD152), Tim3 (also known as HAVCR2), TIGIT (also known as IVSTM3) or OX40. In particular, immunoregulatory molecules correspond to the extracellular domain of receptors, especially the immunoglobulin-like domain of immune checkpoint receptors such as the extracellular or immunoglobulin-like domains of PD1, CTLA-4, Tim3, TIGIT or OX40.

The immunoregulatory molecule may also be a receptor ligand such as PD1-L1 (programmed cell death ligand 1, also known as CD274).

The immunoregulatory molecules can also be cytokines such as IL-2 which is required for the generation and maintenance of Tregs. Also, on dendritic cells, the neutralization of co-stimulation molecules such as CD80, CD86, especially after CTLA4 fixation, can block lymphocyte activation.

Immunoregulatory molecules can exercise their function by modifying the orientation of immune responses, notably towards a Th1, Th9, Th17 profile, for example for the treatment of hypersensitivity responses. In a particular embodiment of the invention, immunoregulatory molecules are molecules capable of activating TLRs (Toll-like receptors). Examples of molecules capable of activating TLRs are molecules comprising structures conserved in pathogens such as flagellins, unmethylated CpG DNA or RNA. For example, viral RNA can stimulate TLR7/TLR8 and flagellin can stimulate TLR5 and thus promote the orientation of responses towards a Th1 profile.

RNA capable of activating TLR, useful in the present invention, can be stabilized against degradation by RNase. In particular viral RNA can be chemically modified compared to natural RNA. The modification may consist of the replacement, insertion or deletion of one or more atoms or groups of atoms. In particular, RNA comprises at least one modified nucleotide. RNA may also include a cap of one or more modified guanosine nucleotides or a tail of several adenosines. The RNA molecules of the present invention are preferentially RNAs comprising between 2 and 1000 nucleotides, more preferentially between 8 and 200 nucleotides even more preferentially between 15 and 31 nucleotides.

The RNA can be single or double-stranded RNA. The RNA useful in the present invention is preferably viral RNA. The viral RNA may be coding or non-coding, preferably the viral RNA is non-coding. In particular, non-coding viral RNA may be derived from cytomegalovirus.

The immunoregulatory molecule may be exposed on the surface of the virus-like particle or may be contained within the virus-like particle.

The immunoregulatory molecule may be exposed to the surface of the virus-like particle, for example via the envelope, a fragment of the envelope, the capsid protein, a fragment of the capsid protein or the transmembrane or anchoring domain of a protein. In particular, the immunoregulatory molecule can be fused through the N-terminal or C-terminal domain of the capsid protein or the capsid fragment of the virus-like particle.

In a particular embodiment, in order to be exposed to the surface of the particle, the immunoregulatory molecule is preferably fused to a transmembrane domain or anchoring domain of a protein, preferably a coat protein, preferably a glycoprotein. The immunoregulatory molecule can be linked to the structural protein or to the transmembrane domain directly or via a "linker", preferably a peptide sequence. Peptide sequence means an amino acid sequence which allows protein subunits to be linked in such a way that the protein adopts a good conformation for the activity of the protein subunits. In particular, the "linker" peptide sequence is a sequence of 1, 2, 3, 4, 5, 10, 15, 20, 30, 40 or 50 amino acids. Preferably, the "linker" peptide sequence is G-G-G-G-S(SEQ ID NO: 3). The immunoregulatory molecule can also be exposed on the surface of the virus-like particle or contained in the particle by means of a chemical or enzymatic reaction.

In a particular embodiment of the invention, the immunoregulatory molecule or the extracellular domain of the immunoregulatory molecule is exposed on the surface of the particle by binding the immunoregulatory molecule or the extracellular domain of the immunoregulatory molecule to the transmembrane domain of the glycoprotein of the VSV-G (vesicular stomatitis virus) or by binding the immunoregulatory molecule or the extracellular domain of the immunoregulatory molecule to the glycophosphatidylinositol (GPI) anchoring domain of the CD59 glycoprotein. Preferably, in order to improve the exposure of the immunoregulatory molecule to the surface of the virus-like particle, the immunoregulatory molecule or the extracellular domain of the immunoregulatory molecule is linked to the glycophosphatidylinositol (GPI) anchoring domain of the CD59 glycoprotein.

The immunoregulatory molecule can be covalently or non-covalently bound, it can be bound directly or via a "linker" to a viral protein, preferably via a peptide sequence. The immunoregulatory molecule can also be linked to the virus-like particle by a chemical or enzymatic reaction.

In a particular example embodiment, a retrovirus-like particle formed by the expression of a Gag protein fused at the C-terminus to an allergen type antigen is provided, further comprising a glycoprotein composed of the transmembrane domain of VSV-G or an anchoring domain of the CD59 glycoprotein fused at the N-terminus to an immunoregulatory molecule such as IL-2, PD-L1 or to the extracellular domain of PD1, or CTLA-4. A linker, preferably a peptide sequence may be included between the two parts to limit stoichiometric constraints. The particle may optionally contain within it non-coding RNA molecules acting as TLR ligands. Virus-like particles can be prepared by the known methods of the art. In particular, they can be produced using encapsidation cell lines. These lines are constructed in vitro and express all the proteins necessary for the constitution and encapsidation of a viral particle. Cell lines can also be transiently transfected with the genetic elements necessary for the constitution of the viral particle. In summary, the method for preparing virus-like particles comprises a step of culturing cell lines expressing the gag and/or pol and/or env proteins as described above, and a step of recovering the particles produced by the cells. The viral particles can be purified for example by centrifugation, gradients, chromatography. The cell supernatant can also be used directly without purification step.

The present invention also relates to one or more plasmid(s) capable of producing in situ the virus-like particle as described above. The plasmid comprises a nucleic acid sequence encoding the modified viral protein of the virus-like particle, for example a nucleic acid sequence encoding an envelope protein and/or a gag protein. In particular, the plasmid comprises a nucleic acid sequence encoding a viral structural protein fused with an antigen. In particular, the plasmid codes for a capsid fused to an antigen. The plasmid may also code for a viral structural protein fused to an immunoregulatory molecule. In particular, the plasmid encodes a transmembrane domain of the VSV-G envelope or a glycophosphatidylinositol anchoring domain of CD59 fused to an immunoregulatory molecule such as IL-2, PD-L1 or the extracellular domain of PD1 or CTLA-4. The viral structural proteins making up the virus-like particle can be encoded by different plasmids. Immunoregulatory molecules may also be encoded by a different plasmid than the structural proteins. Plasmids may also include other elements such as gene markers and/or the origin of replication that allow in vitro manipulations.

Treatment of Immune System Dysfunctions:

The present invention also relates to the virus-like particle as described above or one or more plasmid(s) capable of producing said virus-like particle in situ for use in the treatment of immune dysfunction.

Immune dysfunction refers to diseases caused by an inappropriate response from the immune system. For example, the allergic reaction is an inappropriate response of the immune system to a molecule or combination of molecules exogenous from the environment such as pollens, medicinal products, chemicals or food products. These molecules are called allergens. The allergic reaction is, for example, characterized by a hypersensitivity immune response such as an increase in the production of IgE and/or Th2 T-lymphocytes specific to the allergen.

Pharmaceutical Compositions and Modes of Administration:

The present invention makes advantageous use of a pharmaceutical composition comprising a virus-like particle as previously described or one or more plasmid(s) capable of producing said virus-like particle in situ. The pharmaceutical composition may also include a pharmaceutical excipient such as saline solutions, buffers, isotonic solutes. The composition may also include adjuvants or immunogenic agents.

In general, the composition includes a sufficient quantity of virus-like particles, between $10^3$ and $10^{12}$ particles, more particularly between $10^9$ and $10^{11}$ particles.

The composition can be administered to prevent immune dysfunction, for example before exposure to an allergen in the case of an allergic reaction. Said composition of the present invention may also be administered after the onset of symptoms of immune dysfunction.

The administration of the composition can be done through the different known routes of art which can be adjusted according to antigens, pathology, biological effects, plasmid or particle. For example, the composition may be administered by parenteral injection, such as subcutaneous, intradermal, intravenous, intramuscular and intraperitoneal injection. The composition may also be administered orally, sublingually, by inhalation, by infusion.

According to an embodiment of the invention, the pharmaceutical composition or medicinal product is in solid form. Examples of solid formulations suitable for oral administration include, but are not limited to, granules, powder, capsule, tablet, ointment, gel, dissolving powder, paste, chewing gum, soft capsule or softgel.

The present invention also relates to a method for preventing, treating or reducing immune dysfunction comprising administering to a subject a sufficient amount of a virus-like particle as described above.

The subject is preferably a mammal, preferably a human. In particular this method comprises administering the composition comprising the virus-like particle to a subject.

The present invention will be better understood upon reading the following examples which illustrate the invention without limiting its scope.

Examples

Materials and Methods

Plasmids

The plasmid pGag-pol encoding the capsid of MuLV (murine leukemia virus) is obtained from the plasmid pHIT60 (Soneoka Y et al. Nucleic Acids Research. 1995; 23 (4): 628-633). The CMV promoter is replaced by a minimal CMV promoter comprising a single restriction site (SacII/XbaI) allowing cloning into the plasmid of phCMV expression.

pGagGFP codes for a Gag-GFP fusion protein under the control of an hCMV promoter. This plasmid is obtained from plasmid EPX145-68 (Garrone, P. et al. Sci. Transl. Med. 3, 94ra71-94ra71 (2011)) by inserting a PCR fragment comprising a MluI restriction site between the NruI and NheI sites. The DNA fragment synthesized by PCR and encoding GFP comprising a MluI site in the 5' domain is inserted into the MluI site to give the plasmid CMV-Gag-GFP.

The lentiviral plasmid pcppT.CMV-Gag/OVA encodes a Gag-OVA fusion protein expressed under the control of the human cytomegalovirus (hCMV) promoter and an ampicillin resistance gene. The OVA sequence is inserted into the C-terminal domain of Gag via the unique MluI restriction site (position 8689; made by Genscript®).

pGag-OVA is obtained from vector pcDNA3.1 and codes for the same fusion protein as expressed by pcppT. CMV-Gag/OVA under the control of the hCMV promoter.

Different plasmids encoding different forms of recombinant murine CTLA-4 with specific anchoring sequences were prepared.

The plasmid pCTLA-4WT comprises a coding sequence for the wild-type CTLA-4 protein (NCBI Reference Sequence: nm_009843.4) inserted into the pIRES plasmid (Clontech®) using the EcoRI restriction site (position 1102).

The plasmid pCTLA-4TM codes for the extracellular domain of the murine protein CTLA-4 (SEQ ID NO: 1) (MACLGLRRYK AQLQLPSRTW PFVALLTLLF IPVFS EAIQV TQPSVVLASS HGVASFPCEY SPSHNTDEVR VTVLRQTNDQ MTEVCATTFT EKNTVGFLDY PFCSGTFNES RVNLTIQGLR AVDTGLYLCK VELMYPPPYF VGMGN GTQIY VIDPEPCPDS D F LLWILVAV SLGLFFYSFL VTAV) linked to the transmembrane and intracytoplasmic domains of the VSV-G (vesicular stomatitis virus-derived G) protein (SEQ ID NO: 2: SSIASFFFIIGLIIGLFLVLRVGIHL-CIKLKHTKKRQIYTDIEMNRLGK) and separated from the extracellular domain mCTLA-4 by a flexible G-G-G-G-S sequence (SEQ ID NO: 3).

The plasmid pCTLA-4GPI encodes the extracellular domain of the murine protein CTLA-4 comprising the transmembrane domain of CD59 (SEQ ID NO: 4: MRAQR-GLILLLLLAVFCSTAVSLTCYHCF)

The plasmid pIL-2TM codes for the murine protein IL-2 (GenBank: AAI16874) linked to the transmembrane and intracytoplasmic domain of the VSV-G protein (SEQ ID NO: 1) by a flexible G-G-G-G-S sequence (SEQ ID NO: 3).

The plasmid pIL2GPI encodes the murine IL-2 protein linked to the transmembrane domain of CD59 (SEQ ID NO: 4).

All plasmids are prepared by bacterial culture in TB medium and purified with the "NucleoBond PC 2000 Endotoxin Free" kit (Macherey-Nagel).

Cell Lines.

HEK 293T (CRL-1573, ATCC) cells are cultured at 37° C. at 5% CO2 in DMEM medium supplemented with 2 mM L-glutamine, 100 U/mL penicillin and streptomycin and 10% inactivated fetal calf serum (Thermo Fischer Scientific).

293T-GagOVA cells are obtained by infection of HEK 293T cells with recombinant GagOVA lentiviral particles. The lentiviral particles are produced by transfecting HEK 293T cells with a recombinant GagOVA lentiviral vector ((psi) pcppT.CMV-Gag/OVA), an HIV GagPol plasmid (pCMV9) and a plasmid encoding VSV-g protein (phCMV-VSVg).

Clonal cell lines are obtained by ampicillin selection and limit dilution. Clones expressing eGFP or GagOVA are sorted on GFP fluorescence or by using anti-OVA (Agro-Bio®) and anti-MuLV Gag (clone R187, CRL-1912; ATCC) antibodies in flow cytometry after cell permeation.

Production of Virus-Like Particles (VLP)

Non-recombinant VLP (VLP⁻) or VLP$^{OVA}$ (VLP$^{OVA}$) are produced in 293T or 293T-GagOVA cells, respectively. The cells are seeded in 175-cm³ culture flasks at 15·10⁶ cells per flask and co-transfected to calcium phosphate 24 h later with 50 µg of plasmids comprising pGag-pol.

Tolerogenic non-recombinant VLP or VLP$^{OVA}$ (tVLP, tVLP OVA) are produced in 293T or 293T-GagOVA cells, respectively. The cells are seeded in 175-cm³ culture flasks at 15·10⁶ cells per flask and co-transferred to calcium phosphate 24 hours later with 50 µg of plasmids comprising pGag-pol with pCTLA-4TM or pCTLA-4GPI at a ratio of 3:1 pGag-pol/pCTLA-4 for tolerogenic VLP (tVLP) and a ratio of 1:3 pGag-pol/pCTLA-4 for OVA tVLP.

GFP recombinant VLP are produced in DD7 cells constitutively expressing GagGFP according to the protocol described above.

$VLP_{Il2}$ are produced in 293T cells. The cells are seeded in 175-cm³ culture flasks at 15·10⁶ cells per flask and co-transferred to calcium phosphate 24 hours later with 50 µg of pGag-pol plasmids with or without pIL2™ or $pIL2_{GPI}$ at a ratio of 2:1 pGag-Pol/pIL2.

After 16 or 18 hours, the medium is replaced with DMEM medium-without fetal calf serum.

After 48 hours, the cell supernatant is collected, filtered through 0.45 µm pore membranes and concentrated to obtain a purified solution of retrovirus-like particles (retro VLP). Purification of the filtered supernatant is performed by centrifugation on centricons (Centricon Plus-70, Millipore), then by ultracentrifugation at 107 170 g for 2 hours at 4° C. on a sucrose gradient (Beckman rotor SW41). The VLP are taken up in 1×PBS and their concentration is determined by the BCA method (Pierce BCA Protein, Assay Kit, Thermo scientific).

Immunoprecipitation and Western Blot.

For immunoprecipitation experiments, samples (30 µg total protein) are incubated with 1 µg murine anti-CTLA-4 antibody (clone 14D3, eBiosciences) or 1 µg anti-mIL2 antibody (ebiosciences) at 4° C. for 30 minutes and then mixed with 10 µL of pre-washed Dynabeads® G-protein coupled beads (Thermo Fischer Scientific) for 1 hour. The bead-VLP complexes are washed and the beads removed using glycine buffer (pH=2.6; Sigma Aldrich) prior to analysis by Western blot.

To perform the Western blot, samples (10 µg total VLP proteins or less for recombinant proteins) are mixed with LDS sample buffer and its reducing buffer and then analyzed by electrophoresis in 4-12% Bis Tris Gel according to the supplier's instructions (Thermo Fischer Scientific). The proteins are then transferred to PDVF membranes. Immunostaining is performed in 0.05% PBS Tween buffer with rat anti-mouse antibody (clone R187, CRL-1912 cells; ATCC) recognizing the MuLV p30 Gag capsid, rabbit polyclonal anti-OVA antibody (Agro-Bio).

Biotinylated secondary antibodies and streptavidin-Qdot (Thermo Fischer Scientific) are used for the secondary marker. The signal is detected using Quantum ST4-3026 (Vilber Lourmat).

Mice

Seven-week-old female BALB/C (AnNR/d) mice (Laboratoires Janvier) are kept in the animal housing facility under specific pathogen-free conditions in accordance with the European Union Directive on the protection of animals used for scientific purposes. All protocols were validated by the regional animal experimentation ethics committee.

Tests on Splenic Dendritic Cells.

BALB/c mouse spleens are collected and digested for 30 minutes in RPMI 10% SVF medium (Life technologies) with 0.1 mg/mL of DNase and collagenase IV (Sigma Aldrich). CD3+, CD19+ and Ter119+ cells are removed by magnetic separation with specific biotinylated antibodies (eBiosciences) and anti-biotin beads (30 µL/100.10*6 cells; Miltenyi). The remaining cells are labelled with anti-CD11c and I-A/I-E antibodies and the CD11c+ MHC-II high cells are sorted by flow cytometry (FACS-Aria, BD). The sorted cells are incubated for 24 hours with RPMI+10% SVF+GM-CSF medium (20 ng/ml; Miltenyi)+10 µg/mL LPS (Sigma Aldrich)+VLP at different concentrations. The expression of activation markers (CD80, CD86, CD40, MHC-II) is analyzed by flow cytometry and the level of cytokines secreted into the culture supernatant is tested by ELISA.

Bone Marrow Dendritic Cell Activation Test:

Bone marrow cells collected from the tibia and femur of BALB/c mice are cultured for 8 days in RPMI medium supplemented with 2 mM L-glutamine, 100 U/mL penicillin, 100 µg/mL streptomycin, 10% inactivated fetal calf serum and 20 ng/mL GM-CSF. Every 3 days the medium is replaced. At D8, differentiated bone marrow dendritic cells are cultured for 24 hours in the presence of VLP, LPS, or medium alone as a negative control. The expression of activation markers (CD80, CD86, CD40, MHC-II) is analyzed by flow cytometry and the level of cytokines secreted into the culture supernatant is tested by ELISA.

Murine Model of Food Allergy to Ovalbumin (OVA)

Food allergy to OVA was induced in female BALB/c AnNRj mice by two intraperitoneal injections of 10 µg OVA (A5503; Sigma-Aldrich) formulated with 500 µg aluminum hydroxide (Imject Alum; Thermo Fischer Scientific) one week apart. Three days after sensitization, the mice are injected with 30 µg VLP (total protein) each day for five days. Three days later, the mice are gavaged with 20 mg OVA every two to three days. Food allergy was assessed by a change in core temperature measured within one hour after oral gavage using a rectal probe. Diarrheal stool (score 0 to 3) and shaggy coat (score 0 to 2) were also assessed quantitatively. The allergic severity score (diarrhea score+ coat score) is represented by a maximum score of 5. Mouse serum was collected at different times and stored at −80° C. before analysis by ELISA for immunoglobulin and mMCPT-I.

In vitro proliferation of antigen-specific CD4+ T cells

Splenic cells and mesenteric lymph node cells are taken from OT-II FOXP3-GFP mice expressing GFP specifically in Treg Foxp3+ and a TCR specific for a peptide derived from OVA presented by MHC-II. Non-Treg cells (Tconv; TCR+ GFP⁻) are enriched by negative selection using biotinylated anti-Ter119, CD19 and CD8 antibodies (BD Biosciences) and anti-biotin microbeads (30 µL/100· 10⁶ cells; Miltenyi) and then sorted by flow cytometry (FACS ARIA, BD). The cells are then labelled with the CellTrace Violet marker (OT-II CTV+cells) (CTV, Thermo Fischer Scientific).

The splenic cells containing the dendritic cells are irradiated (25 Gy) and then incubated with the peptide OVA-$II_{323-329}$ (5 µg/mL, Genscript) or an OVA protein (200 µg/mL, Sigma Aldrich) for 1 or 4 hours respectively.

In a 96-well plate, 10⁵ OT-II CTV+ cells or 2D2 CTV+ cells are cultured in RPMI medium supplemented with 2 mM L-glutamine, 100 U/mL penicillin, 100 µg/mL streptomycin, 20 ng/mL GM-CSF (Miltenyi) and 10% fetal calf serum inactivated with 5·10⁵ splenocytes pre-incubated with the antigen in the presence of 1, 5 or 10 µg/mL VLP or tVLP.

After two and three days, the proliferation and activation of Tconv CTV+ cells are analyzed by flow cytometry.

Functional Testing of $VLP_{IL-2}$

The functionality of the $VLP_{IL2}$ has been tested on CTLL-2 cells (ATCC® TIB-214™). The cells are cultured in RPMI medium supplemented with 2 mM L-glutamine, 100 U/mL penicillin and streptomycin, 10% thermally inactivated fetal calf serum, 1% HEPES buffer and 0.1% 2-mercaptoethanol (all from Thermo Fischer Scientific). $VLP_{IL-2}$ (50 µg/mL) or human IL-2 (Proleukin®, Novartis) at desired concentrations are added to the medium. Cell counts and mortality are assessed daily by counting Trypan blue cells in Malassez cells.

Flow Cytometry

The antibodies used in the experiments are listed in Table 1.

TABLE 1 list of antibodies used in flow cytometry.

| Target | Clone | Dilution | Conjugate | Supplier |
|---|---|---|---|---|
| CD4 | RM4-5 | 1:400 | Horizon V500 | eBiosciences |
| CD8 | 53-6.7 | 1:400 | Alexa Fluor 700 | BD |
| IA/IE | M5/114.15.2 | 1:400 | Horizon V500 | BD |
| CD80 | 16-10A1 | 1:400 | PE-Cy7 | eBiosciences |
| CD86 | GL1 | 1:1000 | eFluor 450 | eBiosciences |
| CD11c | N418 | 1:200 | APC | eBiosciences |
| CD25 | PC61.5 | 1:200 | PE-Cy7 | eBiosciences |
| FOXP3 | FJK-16s | 1:100 | FITC | eBiosciences |
| Fixable Viability Dye | | 1:2000 | eFluor 780 | eBiosciences |
| CD40 | HM40-3 | 1:200 | APC | eBiosciences |
| CD11c | N418 | 1:200 | PE | eBiosciences |
| mIL-2 (murine IL-2) | JES6-5H4 | 1:100 | APC | BD |
| CD152 (CTLA-4) | UC10-4B9 | 1:200 | APC | eBiosciences |
| CD3 | 145-2C11 | 1:400 | Biotin | eBiosciences |
| CD19 | MB19-1 | 1:400 | Biotin | eBiosciences |
| Ter-119 | TER-119 | 1:400 | Biotin | eBiosciences |

For in vitro studies, Live Dead eFluor®780 is added to exclude dead cells from the analysis. All flow cytometry experiments are performed on the BC LSRII cytometer and the data are analyzed using FlowJo software (Treestar Inc.).

For flow cytometric analysis of VLP, 20 µg of VLP is incubated with 5 µL of 4 µm diameter aldehyde/sulfate latex beads (Thermo Fischer Scientific) for 15 min at room temperature. PBS is added to a final volume of 1 mL and incubated for 1 hour. The beads are blocked in 20 µL of fetal calf serum for 30 minutes and washed three times and incubated with anti-CD152 or anti-mIL-2 surface antibody (eBiosciences) in PBS, 2% BSA for one hour. For intra-VLP labeling, beads are treated with PBS 1% Triton for one hour. Incubation with the primary antibody (anti-MulV p30, anti-OVA) and a secondary antibody is performed in PBS 0.1% Triton. The beads are then washed and suspended in 200 µL PBS before being analyzed by LSRII flow cytometry (Beckton Dickinson).

ELISA Test mCTLA-4 is detected on the surface of VLP using the ELISA method. The 96-well flat-bottomed plates (Medisorp, Nunc) are coated with murine anti-CD152 antibodies (0.2 µg/mL, clone 14D3, eBioscience) at 4° C. overnight. After washing the wells, the non-specific binding sites are blocked with PBS 1% BSA for 1 hour at room temperature. 90 µL of sample is added to each well with 10 µL Lysis Buffer and incubated for 2 hours at room temperature.

Anti-CD152 mAb antibodies (UC10-4B9, eBioscience), peroxidase-conjugated streptavidin (Sigma-Aldrich) and tetramethylbenzidine (TMB, eBioscience) are added at room temperature for 10 min to detect mCTLA-4. The reaction is stopped by adding 100 µL HCl (1 M) and the optical density is measured at 450 nm with an automatic ELISA reading plate (DTX 880 Multimode Detector, Beckman Coulter). The mCTLA-4-His tag (Thermo Fischer Scientific) is used as standard.

The concentrations of OVA-specific IgE and IgG2A are measured in the serum of sensitized mice using the ELISA method. The 96-well flat-bottomed plates (Nunc, Denmark) are coated with OVA (500 ng/well; Sigma Aldrich) overnight at 4° C. After washing, the non-specific binding sites are blocked with PBS 1% BSA for one hour at room temperature. 100 µL of diluted serum is added to each well and incubated for 2 hours at room temperature. OVA-specific IgE and IgG2A are detected with biotinylated antibodies (Southern Biotech) and revealed with peroxidase-conjugated streptavidin (Sigma Aldrich) and TMB for 5 minutes at room temperature. The reaction is stopped by adding 100 µL HCl (1 M) and the optical density is measured at 450 nm with an automatic ELISA reading plate (DTX 880 Multimode Detector, Beckman Coulter). The level of mMCPT-I is measured using Ready-Set-Go ELISA assays (Thermo Fischer Scientific) following the recommendations of the supplier.

mIL-2 is detected on the surface of VLPs using the Ready-Set-Go mIL-2 (eBiosciences) kits according to the manufacturer's instructions. VLP are used as a negative control.

Statistical Analysis

The statistical analysis is performed with GraphPad Prism (GraphPad software) with the Mann-Whitney U test with *p<0.05 representing a statistically significant difference ( p<0.01; * p<0.001).

Results

1. Validation of OVA and CTLA-4 Expression by $tVLP^{OVA}$

The expression of Gag and OVA by recombinant VLP ($VLP^{OVA}$) has been validated by Western blot. The VLP obtained from WT Gag are used as a control. Western blot analyses of the supernatants of transfected cells show the formation of retro VLP carrying the antigen of interest, in this case ovalbumin (OVA) (FIG. 3A).

Immunoprecipitation by an anti-CTLA-4 antibody shows the assembly of immunoregulatory molecules (CTLA-4) on $tVLP^{OVA}$ (revealed with an anti-Gag; FIG. 3B).

The expression of the different chimeric forms of CTLA-4 (WT, TM-VSVG or with the GPI anchoring domain) was compared in transfected cells or on VLP by flow cytometry. Non-transfected cells or VLP were used as a negative control. After comparison of the level of expression of the different chimeric forms of CTLA-4 (FIG. 3C), it appears that the GPI (CD59b) system is optimal and will be retained in the following results. We were able to quantify the presence of the CTLA-4 domain in our preparations using ELISA and the molecule represents between 8 and 15% of the total proteins measured using the bicinchoninic acid (BCA) method (FIG. 3D).

2. In Vitro Evaluation of the Effect of $tVLP^{GFP}$ on Dendritic Cell Activation $tVLP^{GFP}$ or $VLP^{GFP}$ (without CTLA4) and VLP controls were contacted with purified dendritic cells (DC) based on CD11c and MHC-IIhi expression from BALB/c mouse splenocytes (FIG. 4A). The uptake of tVLP$^{GFP}$ by purified dendritic cells is confirmed by the presence of GFP+ cells after 24 hours of culture. VLP are used as a negative control (FIG. 4B). The DC phenotype is then analyzed 24 hours after stimulation by LPS (TLR4 ligand). The results show that only tVLP$^{GFP}$ significantly and dose-dependently block the LPS-induced increase in expression of co-stimulation molecules (CD80, CD86) (FIGS. 4C-4E). Interestingly, the level of expression of MHC-II molecules is unaffected, not interfering with the ability of DC to present the antigen (FIG. 4E). Similar results were observed when DC are derived from bone marrow progenitor cells (FIG. 5A). An increase in the level of IL-10 could also be detected in the medium in the presence of tVLP$^{GFP}$, indicating immunoregulation directly on the dendritic cells (FIG. 5B).

3. In Vitro Evaluation of the Effect of tVLP-on the Activation of Antigen-Specific T Cells.

We evaluated whether tVLP were able to block the activation of CD4+CD25-T-lymphocytes from antigen-specific (OVA) OT-II mice after contact with DC, present among splenocytes irradiated and loaded with OVA protein or OVA$_{323-339}$ peptide (FIG. 6A). Analysis of T cell proliferation with "celltrace" violet (CTV®) shows good activation of OT-II T cells in the presence of OVA$_{323-339}$ peptide alone or peptide plus VLP- (FIG. 6B). On the other hand, the addition of tVLP leads to a significant suppression of T cell activation with a dose-dependent effect, reaching at day 3 about 80% suppression with peptide stimulation (FIG. 6C) and 40% suppression with protein. Interestingly, the immunoregulatory action of tVLP is more effective when compared to Abatacept (hCTLA-4-Ig) treatment in equivalent amounts.

4. Protective Effect of tVLP$^{OVA}$ in the Occurrence of Food Allergy.

Five groups of mice were sensitized at D-14 and -7 to OVA and treated daily for 5 days intraperitoneally with VLP-, VLP$^{OVA}$, tVLP$^{OVA}$, tVLP- or VLP$^{OVA}$+hCTLA-4 (50 µg/gavage). At D10, mice are gavaged every other day by oral administration of OVA and the severity of allergic reactions is measured after the fifth gavage (FIG. 7A). The mice were then re-gavaged with OVA every 9 to 12 days until a score above 4 was obtained for 80% of the mice in the control group. At D33 and D45, peripheral blood was collected 30 min after sensitization. The level of MCPT-1 in peripheral blood is measured at D33 and the percentage of ICOS+Tregs (CD4+, CD25+, Foxp3+) is measured at D45 (FIGS. 7C and 7D).

Food allergy was assessed by a change in core temperature measured within one hour after oral feeding. Diarrheal stool (score 0 to 3) and shaggy coat (score 0 to 2) were assessed quantitatively. Allergic severity scores (diarrhea score and coat score) for different mice are shown in FIG. 7B. It was observed that 5 days of treatment with tVLP$^{OVA}$ is sufficient to control severe allergic reactions on a long-term basis (FIG. 7B). Indeed, during the first challenge cycle (D24), no mice among the 8 in the tVLP$^{OVA}$ group showed severe hypothermia (Δ<-2° C.; 0/8) while almost half of the mice treated with VLP$^{OVA}$ control showed a drop in temperature and strong clinical symptoms. It should be noted that VLPs lacking an immunoregulatory molecule (VLP$^{OVA}$) or antigen (tVLP-) do not show therapeutic efficacy. Subsequent challenge cycles confirm the maintenance of this regulation over the long term since at D160, alone in the tVLP$^{OVA}$ group, none of the mice reached a score >2 and a temperature drop <-2° C.

5. Therapeutic Action of tVLP$^{OVA}$ Correlates with the Recruitment of Regulatory T-Lymphocytes We were able to identify a mechanism involved in immunoregulation to control allergic responses. Indeed, we were able to show that the tolerogenic action of tVLP$^{OVA}$ is linked to the recruitment of regulatory T-lymphocytes. For this purpose, mice treated with tVLP, tVLP$^{OVA}$ or tVLP-control were euthanized and regulatory T-lymphocytes were purified and injected into naïve BALB/c recipient mice, which were then sensitized to OVA and subjected to several challenge tests (FIG. 8A). After several challenges, we can observe that the transfer of regulatory T-lymphocytes from mice treated with tVLP$^{OVA}$ protects the mice from severe allergic reactions throughout the study (FIGS. 8B and 8C). It should be noted that the transfer of mice treated with tolerogenic but antigen-empty retro VLP (tVLP) has no therapeutic action, demonstrating the specificity of action exerted by tVLP$^{OVA}$.

6. Validation of IL-2 Expression by VLP$_{IL2}$

The expression of Gag and IL-2 by recombinant VLP (VLP$_{IL2}$) has been validated by Western blot. VLP- obtained from WT Gag and murine IL-2 are used as controls. Western blot analyses of transfected cell supernatants indicate the formation of VLP expressing IL-2 (FIG. 9A).

The presence of IL-2 was quantified using ELISA on VLP$_{IL2}$ and VLP (FIG. 9B). The expression of the different chimeric forms of IL-2 (TM-VSVG or with the GPI anchoring domain) was compared in transfected cells or on VLP by flow cytometry (FIG. 9C). Non-transfected cells or VLP were used as a negative control. After comparison of the level of expression of the different chimeric forms of VLP$_{IL2}$ (FIG. 9C), the GPI (CD59b) system was found to be optimal.

7. Functional effect of VLP$_{IL2}$

Cell proliferation and percent CTLL-2 cell mortality were measured by Trypan blue in Malassez cells in the presence of IL-2 at 25 IU/mL, 50 IU/mL, VLP$_{IL2}$ or in the absence of IL-2 (SS IL-2).

Cell proliferation and the percentage of CTLL-2 cell mortality in the presence of VLP$_{IL2}$ are similar to the results obtained in the presence of cytokine IL-2 indicating that VLP$_{IL2}$ cells allow CTLL-2 cells to proliferate and are therefore functional (FIGS. 10A and 10B).

The invention claimed is:

1. A synthetic retroviral particle comprising an antigen and an immunoregulatory molecule exposed on the surface of the synthetic retroviral particle, said antigen being an allergen, wherein the immunoregulatory molecule exerts suppressive functions on antigen presenting cells, thereby promoting recruitment of regulatory T cells, and the immunoregulatory molecule is linked to the transmembrane glycoprotein domain of vesicular stomatitis virus (VSV-G) or to the glycophosphatidylinositol (GPI) anchoring domain of the CD59 glycoprotein.

2. The synthetic retroviral particle according to claim 1, wherein the immunoregulatory molecule is an immune checkpoint receptor.

3. The synthetic retroviral particle according to claim 2, wherein the immunoregulatory molecule comprises the extracellular domain of said receptor.

4. The synthetic retroviral particle according to claim 1, wherein the immunoregulatory molecule is selected from the group consisting of interleukin 2 (IL-2), interleukin 10 (IL-10) and transforming growth factor beta (TGF-beta).

5. A method for treating an allergy in a subject, wherein the subject is administered with the synthetic retroviral particle of claim 1.

6. The method of claim 5, wherein the allergy is a food allergy, the allergen being contained in or derived from a food.

7. The method of claim 6, wherein the food is selected from milk, eggs, sesame, wheat, soy, fish, seafood, peanuts, and nuts.

8. The method of claim 5, wherein said synthetic retroviral particle is in the form of a pharmaceutical composition further comprising a pharmaceutical excipient.

9. A pharmaceutical composition comprising a plasmid or set of plasmids comprising nucleic acid sequences encoding the allergen, the immunomodulatory molecule, and viral proteins required for production of the synthetic retroviral particle according to claim 1 in a host cell.

10. A method for treating an allergy in a subject, wherein the subject is administered with the pharmaceutical composition of claim 9.

11. The method according to claim 10, wherein the allergy is a food allergy, the allergen being contained in or derived from a food.

12. The method according to claim 11, wherein the food is selected from milk, eggs, sesame, wheat, soy, fish, seafood, peanuts, and nuts.

13. The synthetic retroviral particle according to claim 2, wherein the immune checkpoint receptor is selected from the group consisting of cytotoxic T-lymphocyte-associated protein 4 (CTLA4), programmed cell death 1 (PD-1), T-cell immunoglobulin and mucin domain 3 (Tim-3), T cell immunoreceptor with immunoglobulin and ITIM domains (TIGIT), lymphocyte activation gene 3 (LAG-3), and tumor necrosis factor receptor superfamily, member 4 (OX40).

* * * * *